United States Patent [19]

Stein et al.

[11] Patent Number: 5,567,752
[45] Date of Patent: Oct. 22, 1996

[54] SILICON- AND NITROGEN- CONTAINING ADHESION PROMOTORS AND COMPOSITIONS CONTAINING THEM

[75] Inventors: Judith Stein, Schenectady; Jeffrey H. Wengrovius, Scotia; Paul R. Willey, Clifton Park, all of N.Y.

[73] Assignee: General Electric Company, Schenectady, N.Y.

[21] Appl. No.: 562,276

[22] Filed: Nov. 22, 1995

Related U.S. Application Data

[63] Continuation-in-part of Ser. No. 395,129, Feb. 27, 1995, abandoned.

[51] Int. Cl.$^6$ ........................................ C08K 5/54
[52] U.S. Cl. .................. 524/188; 428/447; 524/730; 524/731; 524/702; 524/703; 524/783; 524/785; 524/779; 524/789; 524/786; 556/413; 556/425
[58] Field of Search ........................... 524/188, 730, 524/731, 783, 785, 789, 779, 703, 702, 786; 428/447; 556/413, 425

[56] References Cited

U.S. PATENT DOCUMENTS 3,837,876  9/1974  Mayuzumi et al. .
4,694,093  9/1987  Sugimori et al. .
4,727,168  2/1988  Yoshino et al. .
5,475,044  12/1995  Stein .................................. 524/188

FOREIGN PATENT DOCUMENTS 0320861  6/1989  European Pat. Off. .
52065529  5/1988  Japan .
57044690  4/1990  Japan .
04268385  11/1991  Japan .

Primary Examiner—Melvyn I. Marquis
Attorney, Agent, or Firm—William H. Pittman

[57] ABSTRACT

Silicon- and nitrogen-containing compositions prepared by the reaction of an aminoalkylsilane such as 3-aminopropyl- or 3-methylaminopropyltrimethoxysilane with a glycidoxyalkylsilane such as 3-glycidoxypropyltrimethoxysilane are useful as adhesion promoters in addition curable polyorganosiloxane compositions. The latter are illustrated by mixtures of vinyl-substituted polyorganosiloxanes and hydride polyorganosiloxanes, also containing at least one platinum group metal compound as a hydrosilylation catalyst.

14 Claims, No Drawings

SILICON- AND NITROGEN- CONTAINING ADHESION PROMOTORS AND COMPOSITIONS CONTAINING THEM

CROSS-REFERENCE TO RELATED APPLICATIONS

This application is a continuation-in-part of application Ser. No. 08/395,129 filed Feb. 27, 1995, abandoned.

BACKGROUND OF THE INVENTION

This invention relates to polyorganosiloxane compositions. More particularly, it relates to addition curable polyorganosiloxanes and still more particularly to materials having improved adhesion to metal and plastic substrates.

The use of polyorganosiloxanes (hereinafter sometimes "silicones") in the form of elastomeric compositions is now widespread. Elastomeric silicones include room temperature vulcanizable compositions, which cure upon standing in the presence of moisture, and addition curable compositions, which cure rapidly upon heating.

Addition curable silicones are of particular use when rapid cure is desirable or when the presence of moisture or, ultimately, of the by-products formed during the curing of room temperature vulcanizable materials is not desired. Illustrative uses are as potting compounds, in sealed environments in which water is not tolerated or in electronic applications. Curing of the addition curable silicones may be by direct heating or by an equivalent means such as ultrasound.

For such electronic applications as insulating coatings for circuit boards, elastomeric silicones in the form of conformal coatings are often preferred. Such coatings are resistant to high temperature and high humidity conditions, in addition to being electrically insulating.

Cured silicone elastomers prepared from addition curable compositions are frequently lacking in adhesion to metal and plastic substrates. Thus, improvement of their adhesion is very desirable. While the use of high curing temperatures, typically 100° C. or greater, is tolerable for elastomeric coatings on metal substrates, substantially lower curing temperatures, ordinarily no higher than 85° C., are frequently required in the case of resinous and especially thermoplastic substrates to avoid heat-induced distortion. The problem of low adhesion is even greater in the case of curing at such low temperatures. At room temperature (i.e., about 25° C.), curing is generally so slow as to be commercially unfeasible.

The present invention includes adhesion promoting compositions for addition curable silicones which, when incorporated in said silicones, are effective with both metal and plastic substrates and, depending on molecular structure, at both low and high curing temperatures, often including room temperature. Said adhesion promoters are suitable for use in such specialized silicone compositions as conformal coatings.

SUMMARY OF THE INVENTION

In one of its aspects, the invention includes silicon- and nitrogen-containing compositions which are the reaction products of at least one aminoalkylsilane of the formula

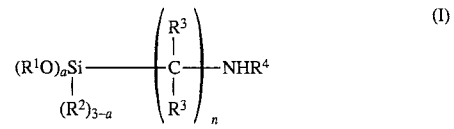

with at least one glycidoxyalkylsilane of the formula

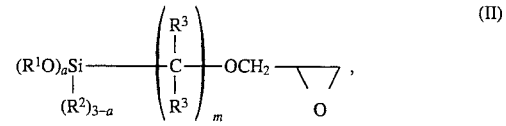

wherein each of $R^1$ and $R^2$ is independently $C_{1-8}$ alkyl; each $R^3$ is independently hydrogen or $C_{1-4}$ primary or secondary alkyl; $R^4$ is hydrogen, $C_{1-4}$ primary or secondary alkyl or $C_{6-10}$ aryl or alkaryl; each a is independently 1–3 and each of m and n is independently 2 or 3.

Another aspect of the invention is an addition curable composition comprising a mixture of:

(A) at least one polyorganosiloxane having alkenyl groups bonded to silicon;

(B) at least one hydride polyorganosiloxane comprising at least one organosiloxane unit having an Si—H moiety;

(C) as a catalyst, at least one platinum group metal compound in an amount effective to cause hydrosilylation of reagent A with reagent B; and (D) an adhesion promoting proportion of a silicon- and nitrogen-containing composition as defined hereinabove.

Still another aspect is an article comprising a metal or plastic substrate having a coating of an addition curable composition as described above.

DETAILED DESCRIPTION; PREFERRED EMBODIMENTS

In the aminoalkylsilanes of formula I which are employed as reagents for the preparation of the silicon- and nitrogen-containing compositions of the invention, each $R^1$ and $R^2$ radical is $C_{1-8}$ alkyl, preferably $C_{1-2}$ primary alkyl and most preferably methyl. Each $R^3$ may independently be a hydrogen atom or $C_{1-4}$ primary or secondary alkyl radical; preferably all $R^3$ values are hydrogen. The value of a is 1–3 and preferably 3; n may be 2 or 3 and is usually 3.

The $R^4$ radical may be hydrogen, $C_{1-4}$ primary or secondary alkyl or $C_{6-10}$ aryl or alkaryl. It is preferably hydrogen or methyl, depending on the intended use of the silicone- and nitrogen-containing composition as explained hereinafter. Thus, the preferred aminoalkylsilanes are 3-aminopropyltrimethoxysilane and 3-methylaminopropyltrimethoxysilane.

The glycidoxyalkylsilanes of formula II contain $R^{1-2}$ and $R^3$ radicals defined in the same way as those in the compound of formula I, with the same or analogous preferences. Thus, the preferred compound of formula II is 3-glycidoxypropyltrimethoxysilane.

Reaction between the aminoalkylsilane and the glycidoxyalkylsilane may be conducted by simply heating the two reagents at a temperature in the range of about 50°–100° C. Approximately equimolar proportions of the two reagents are normally used, with the proviso that it is generally preferred to employ a slight excess of glycidoxyalkylsilane if the aminoalkylsilane is a primary amine, since residues of primary amine in the product will inhibit hydrosilylation of the addition curable composition. In general, a molar ratio of glycidoxyalkylsilane to aminoalkylsilane in the range of about 0.9–1.2:1 is employed.

Following completion of the reaction, which generally requires on the order of 3–5 hours, volatiles may be removed by conventional means such as vacuum stripping.

The molecular structures of the silicon- and nitrogen-containing compositions of this invention are not known with certainty. Analysis by proton nuclear magnetic resonance spectroscopy and gas chromatograph-mass spectroscopy suggests that an initial attack of the amino group on the epoxy group may take place to form an intermediate hydroxy compound, which can then displace an alkoxy group on silicon in the same or another molecule. If the displaced alkoxy group is attached to the aminoalkyl silicon, the product would then have the formula

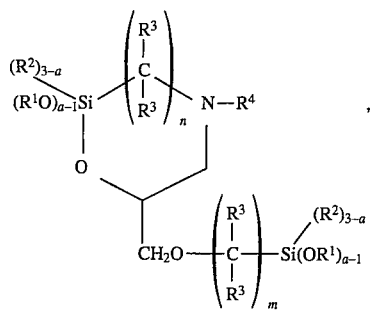

wherein $R^{1-4}$, a, m and n are as previously defined. However, because of the possibility of other structures including condensation products involving several molecules of the intermediate, the compositions are best defined in terms of the method for their preparation.

The preparation of the silicon- and nitrogen-containing compositions of this invention is illustrated by the following examples.

EXAMPLE 1

A 50-ml. round-bottomed flask was charged with 1.75 grams (9.8 mmol.) of 3-aminopropyltrimethoxysilane and 2.62 grams (11.1 mmol.) of 3-glycidoxypropyltrimethoxysilane. The mixture was heated for 4 hours at 70° C., after which volatiles were removed in vacuum. The desired silicon- and nitrogen-containing composition was obtained as a yellow oil.

EXAMPLE 2

By the procedure of Example 1, a reaction was conducted between 3.92 grams (20.3 mmol.) of 3-methylaminopropyltrimethoxysilane and 4.6 grams (19.5 mmol.) of 3-glycidyoxypropyltrimethoxysilane. A similar product was obtained.

As previously mentioned, the silicon- and nitrogen-containing compositions of this invention are useful as adhesion promoters in addition curable silicon compositions. Said compositions comprise reagents A, B and C as previously defined, in combination with reagent D, the adhesion promoter.

Both one-part and two-part addition curable compositions are included as part of the invention. One-part compositions generally include reagents A–D in combination with inhibitors which suppress curing at ambient temperature; suitable inhibitors are disclosed hereinafter. In two-part compositions, the hydrosilylation catalyst is separated from any combination of reagents A and B prior to the time curing is desired.

Reagent A is at least one polyorganosiloxane having alkenyl, most often $C_{1-3}$ alkenyl and preferably vinyl groups, bonded to silicon. Such silicone materials are well known in the art and have been employed previously in the preparation of cured silicone materials. They are described, for example, in U.S. Pat. Nos. 4,418,157, 4,851,452 and 5,011,865, the disclosures of which are incorporated by reference herein.

A typical linear (polydiorganosiloxane) silicone material useful as reagent A is represented by the formula

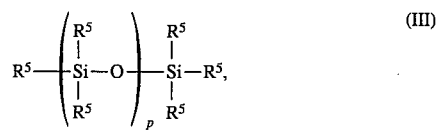

(III)

wherein each $R^5$ is independently $C_{1-6}$ alkyl, phenyl, 3,3,3-trifluoropropyl or vinyl and p has a value such that the viscosity of the silicone is in the range of about 100–1,000,000 and preferably about 3,000–95,000 centipoise at 25° C. Most often, each $R^5$ that is not vinyl is methyl.

An art-recognized convention for designating silicone structural units in accordance with the number of oxygen atoms attached to silicon is employed herein. That convention uses the letters M, D, T and Q to designate said number of oxygen atoms as abbreviations for "mono", "di", "tri" and "quatro". Thus, the silicone of formula III consists of M end groups and D internal units. The presence of T and/or Q units imparts branched and/or crosslinked structure to the compound.

As further used herein, expressions such as "M(vinyl)" and "D(hydrogen)" denote an appropriate unit respectively having one vinyl group or one hydrogen atom attached to silicon. Generically, however, proportions of M (etc.) units include such analogous units as M(vinyl). The particularly preferred silicones of formula I are those in which the vinyl groups are attached to terminal silicon atoms.

The proportion of M, D, T and Q units in reagent A and in the mixture as a whole may be varied to afford a composition of the desired degree of branching and other properties. Thus, for example, the aforementioned U.S. Pat. No. 4,418,157 describes a base silicone material which may contain vinyl groups bonded to silicon and which has prescribed proportions of M, D and Q units.

For the purposes of the present invention and especially for use as a conformal coating composition, it is often preferred that at least about 10% and preferably about 25–40% by weight of reagent A comprise compounds with a high proportion of Q units. More specifically, the ratio of combined M and D units (including vinyl- and hydrogen-substituted units) to Q units in such compounds is at most about 0.75:1 and preferably about 0.3–0.7:1. Most preferably, only M and Q units are present. Compounds having these proportions have sufficient crosslinking and/or branching to serve adequately as conformal coatings. Such compounds may be prepared by art-recognized methods, such as the reaction of a silica hydrosol with an alkyl silicate or alkylchlorosilane containing one or more alkyl groups per molecule.

In general, reagent A comprises principally or, preferably, entirely compounds in which vinyl groups are bonded to terminal silicon atoms on the silicone chain.

Reagent B may be represented by a linear polysiloxane of the formula

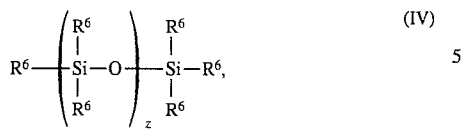

wherein each $R^6$ is independently $C_{1-6}$ alkyl, phenyl, 3,3,3-trifluoropropyl or hydrogen. The polysiloxane of formula IV comprises M and D units, but reagent B may also typically contain Q units.

Most often, reagent B has an average of no more than one hydrogen atom bonded to any silicon atom and any non-hydrogen $R^6$ values are methyl. It usually contains about 0.02–2.0% (by weight) silicon-bonded hydrogen.

Reagent C is at least one platinum group catalyst. By "platinum group" is meant the portion of Group VIII of the Periodic Table, as traditionally identified, containing the metals rhodium, ruthenium, palladium, osmium, iridium and platinum. The preferred metals from this group are rhodium, palladium and platinum, with platinum being particularly preferred because of its relative availability and particular suitability.

Numerous types of platinum catalysts are known in the art and are disclosed in the patents incorporated by reference hereinabove. They include, for example, reaction products of chloroplatinic acid with olefins, alcohols, ethers, aldehydes and vinylsiloxanes such as tetramethyldivinyldisiloxane. A reaction product of chloroplatinic acid with tetramethyldivinyldisiloxane in the presence of sodium bicarbonate as disclosed in U.S. Pat. No. 3,775,452, dissolved in xylene to a level of about 5% by weight platinum, is often preferred; it is hereinafter designated "Karstedt's catalyst".

The addition curable compositions of this invention may contain other constituents such as fillers and inhibitors which suppress premature curing. Suitable fillers include extending fillers such as quartz, aluminum oxide, aluminum silicate, zirconium silicate, magnesium oxide, zinc oxide, talc, diatomaceous earth, iron oxide, calcium carbonate, clay, titania, zirconia, mica, ground glass, glass fiber, sand, carbon black, graphite, barium sulfate, zinc sulfate, wood flour, cork and fluorocarbon polymer powder. Also included are reinforcing fillers such as fumed silica and precipitated silica, particularly silica which has been treated with an organohalosilane, a disiloxane and/or a disilazane.

Inhibitors include volatile materials, non-volatile materials or both. Illustrative non-volatile inhibitors are esters of olefinic dicarboxylic acids, as illustrated by dibutyl maleate. Various acetylenic alcohols such as methylbutynol and dimethylhexynol, as well as more volatile maleates such as dimethyl maleate, may be used as volatile inhibitors.

In general, about 1–20 parts by weight of reagent B are present in the compositions of this invention per 100 parts of reagent A, which is the basis for all proportions not otherwise defined herein. Reagent C, the hydrosilylation catalyst, is present in a catalytic amount, typically at least about 0.1 and most often about 5–100 ppm of platinum group metal. Reagent D is present in an adhesion promoting amount, most often about 0.3–2.0 parts. Reinforcing and extending fillers, when present, are typically in an amount up to about 50 parts and about 200 parts, respectively. In the case of compositions in which reagent A does not contain a substantial proportion of Q units, the presence of the reinforcing filler may be mandatory.

The compositions of this invention may be prepared by simply blending the constituents. If a two-part composition is desired, one part contains the hydrosilylation catalyst and the other part contains all of either reagent A or, usually, reagent B. Inhibitors are present in one-part compositions and may also be present in two-part compositions, typically in the amount of about 0.01–2.0 parts per 100 parts of reagent A.

In general, the compositions of this invention in which $R^3$ is hydrogen are useful as adhesion promoters for application to both plastic and metal substrates under high temperature (typically at least about 85° C.) curing temperatures. Compositions in which $R^3$ is alkyl, especially methyl, are typically employed in conformal coatings and for curing at temperatures below about 85° C., most often at least about 50° and preferably about 50°–75° C.

The compositions of this invention may be applied to a substrate, typically metal or plastic, by conventional methods such as roller coating, extrusion, brush coating or the like. It is generally preferred to clean the substrate before application of the composition, typically by treatment with aqueous base or a solvent in the case of plastic substrates and with a conventional cleaner in the case of metals.

The preparation and use of the addition curable compositions of this invention is illustrated by the following examples.

EXAMPLE 3

A conformal coating composition was made from two separately prepared mixtures.

Mixture A—1200 parts of a vinyl-terminated polydimethylsiloxane having a viscosity of 750 centipoise, 300 parts of a vinylpolydimethylsiloxane having 87% (by number) M units and 13% M(vinyl) units and a molar ratio of total M units to Q units of about 0.5, and 102 parts of a polymethylsiloxane having M, D, M(hydrogen) and D(hydrogen) units with about 0.76% silicon-bonded hydrogen.

Mixture B—9 parts of the product of Example 2, 0.17 part of Karstedt's catalyst and 1.35 parts of dibutyl maleate, mixed and allowed to stand for 2 hours prior to use.

A blend of 100 parts of mixture A, 1.17 parts of mixture B and 0.042 part of methylbutynol inhibitor was prepared. Prior to curing, its shelf life was longer than 3 days at 50° C.

The blend was coated on a circuit board and cured at 85° C. for 10 minutes After curing, the coating adhered to the surface board and could not be removed by scratching with a fingernail. It did not cause corrosion of the board upon exposure for 28 days at 95° C. to an atmosphere containing 95% relative humidity.

EXAMPLE 4

One-part formulations were prepared by blending 10.4 grams of a polydimethylsiloxane having terminal vinyl-containing units and a viscosity of about 40,000 centipoise, 2.6 grams of fumed silica treated with hexamethyldisilazane and hexamethylcyclotrisiloxane, 2.7 microliters of Karstedt's catalyst, 1 microliter of 3,5-dimethyl-1-hexyn-3-ol, 0.12 gram of the product of Example 1 or 2 and 0.23 gram of a polymethylsiloxane having about 0.8% silicon-hydrogen bonds. The mixtures were degassed by two cycles of evacuation and centrifugation, after which they were employed in the preparation of lap shear specimens in accordance with ASTM method D3983, using substrates of steel, aluminum or bisphenol A polycarbonate. The specimens were cured and tested as listed in the following table.

| Adhesion Promoter | Substrate | Cure conditions Time, hrs. | Cure conditions Temp., °C. | Failure mode* | Lap shear strength, kg./cm.² |
|---|---|---|---|---|---|
| None (control) | Steel | 1 | 100 | A | — |
|  | Al | 1 | 100 | A | — |
|  | PC | 1 | 100 | A | — |
| Ex. 1 | Steel | 1 | 100 | C | 19.0 |
|  | Al | 1 | 100 | C | 21.1, 25.6 |
|  | PC | 1 | 100 | C | 18.6 |
| Ex. 2 | Steel | 1 | 70 | C | 17.3 |
|  | Al | 1 | 70 | C | 19.0 |
|  | PC | 1 | 100 | A | — |
|  | Steel | 48 | 25 | C | 19.5, 20.7 |
|  | Al | 48 | 25 | C | 27.4 |

*A - adhesive,
C = cohesive.

It will be seen that while the controls employing no adhesion promoter uniformly failed adhesively (i.e., between the cured composition and the substrates) and therefore no lap shear strength could be determined, all but one of the specimens employing metal substrates and the silicon- and nitrogen-containing compositions of this invention failed cohesively. Cohesive failure was observed with the product of Example 1 on polycarbonate, although the product of Example 2 failed adhesively under the same conditions. Thus, the effectiveness of the silicon- and nitrogen-containing compositions as adhesion promoters under various conditions is apparent.

What is claimed is:

1. An addition curable composition comprising a mixture of:

(A) at least one polyorganosiloxane having alkenyl groups bonded to silicon;

(B) at least one hydride polyorganosiloxane comprising at least one organosiloxane unit having an Si—H moiety;

(C) as a catalyst, at least one platinum group metal compound in an amount effective to cause hydrosilylation of reagent A with reagent B; and (D) an adhesion promoting proportion of a silicon- and nitrogen-containing composition which is the reaction product of at least one aminoalkylsilane of the formula

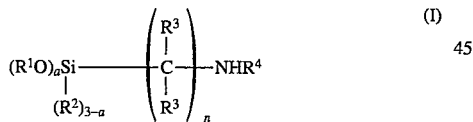

(I)

with at least one glycidoxyalkylsilane of the formula

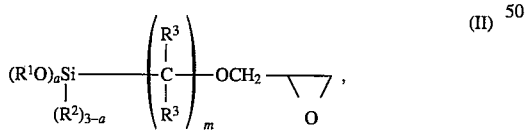

(II)

wherein each of $R^1$ and $R^2$ is independently $C_{1-8}$ alkyl; each $R^3$ is independently hydrogen or $C_{1-4}$ primary or secondary alkyl; $R^4$ is hydrogen, $C_{1-4}$ primary or secondary alkyl or $C_{6-10}$ aryl or alkaryl; each a is independently 1–3 and each of m and n is independently 2 or 3.

2. A composition according to claim 1 wherein the alkenyl groups are vinyl groups.

3. A composition according to claim 2 wherein reagents A and B are polymethylsiloxanes.

4. A composition according to claim 3 wherein the platinum group metal is platinum.

5. A composition according to claim 3 which is a one-part composition.

6. A composition according to claim 5 wherein reagent A comprises a polymethylsiloxane comprising M and D units and having vinyl groups attached to the terminal silicon atoms.

7. A composition according to claim 6 which also contains a reinforcing filler.

8. A composition according to claim 5 wherein reagent A comprises a polymethylsiloxane comprising M and D units and having vinyl groups attached to the terminal silicon atoms, in admixture with about 25–40% based on reagent A of a polymethylsiloxane comprising M and Q units in a ratio in the range of about 0.3–0.7:1.

9. A composition according to claim 3 which is a two-part composition.

10. A composition according to claim 3 wherein each $R^1$ and each $R^2$ is methyl.

11. A composition according to claim 10 wherein each $R^3$ is hydrogen.

12. A composition according to claim 11 wherein each a is 3 and each of m and n is 3.

13. A composition according to claim 12 wherein $R^4$ is hydrogen or methyl.

14. An article comprising a metal or plastic substrate having a coating of an addition curable composition comprising a mixture of:

(A) at least one polyorganosiloxane having alkenyl groups bonded to silicon;

(B) at least one hydride polyorganosiloxane comprising at least one organosiloxane unit having an Si—H moiety;

(C) as a catalyst, at least one platinum group metal compound in an amount effective to cause hydrosilylation of reagent A with reagent B; and (D) an adhesion promoting proportion of a silicon- and nitrogen-containing composition which is the reaction product of at least one aminoalkylsilane of the formula

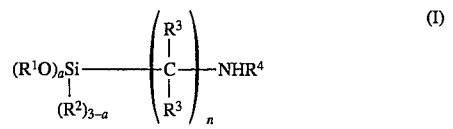

(I)

with at least one glycidoxyalkylsilane of the formula

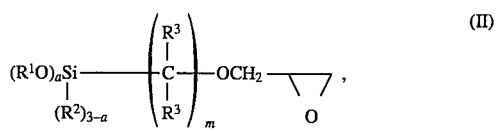

(II)

wherein each of $R^1$ and $R^2$ is independently $C_{1-8}$ alkyl; each $R^3$ is independently hydrogen or $C_{1-4}$ primary or secondary alkyl; $R^4$ is hydrogen, $C_{1-4}$ primary or secondary alkyl or $C_{6-10}$ aryl or alkaryl; each a is independently 1–3 and each of m and n is independently 2 or 3.

* * * * *